United States Patent [19]
Thomashow et al.

[11] Patent Number: 5,892,009
[45] Date of Patent: Apr. 6, 1999

[54] DNA AND ENCODED PROTEIN WHICH REGULATES COLD AND DEHYDRATION REGULATED GENES

[75] Inventors: Michael F. Thomashow; Eric J. Stockinger, both of East Lansing, Mich.

[73] Assignee: Michigan State University, East Lansing, Mich.

[21] Appl. No.: 706,270

[22] Filed: Sep. 4, 1996

[51] Int. Cl.[6] .............................. C07H 21/02; C07K 1/00; A01N 37/18

[52] U.S. Cl. ..................... 536/22.1; 536/23.6; 530/350; 530/370; 530/379; 514/2; 514/12; 800/278

[58] Field of Search ................................. 536/22.1, 23.6; 514/2, 12; 530/350, 370, 379; 800/278

[56] References Cited

U.S. PATENT DOCUMENTS

| | | | |
|---|---|---|---|
| 5,296,462 | 3/1994 | Thomashow | 514/2 |
| 5,356,816 | 10/1994 | Thomashow | 435/320.1 |

OTHER PUBLICATIONS

Guy, C.L., Annu.Rev.Plant Physiol. Plant Mol.Biol. 41:187–223 (1990).
Monroy, A.F. et al., Plant Physiol., 102:1227–1235 (1993).
Monroy, A.F. et al., The Plant Cell, 7:321–331 (1995).
Knight et al., The Plant Cell, 8:489–503 (1996).
Knight, M.R. et al., Nature, 352:524–526 (1991).
Ding, J.P. et al., Plant J., 3:713–720 (1993).
White, T.C. et al., Plant Physiol., 106:917–928 (1994).
Hajela, R.K. et al., Plant Physiol., 93:1246–1252 (1990).
Gilmour, S.J., Plant Physiol., 87:745–750 (1988).
Schiestl, R.H. et al., Current Genetics, 16:339–346 (1989). (Abstract).
Berger, S.L. et al., Cell, 70:251–265 (1992).
Stockinger, E.J., et al., J. Heredity, 87:214–218 (1996). (Abstract).
Walling, L. et al., Nucleic Acids Res., 16:10477–10492 (1988). (Abstract).
Raikhel, N., Plant Physiol., 100:1627–1632 (1992).
Hahn, S., Cell 72:481–483 (1993).
Foster et al., FASEBJ, 8:192–200 (1994).
Ma, J. et al., Cell, 51:113–199 (1987).
Ma, J. et al., Nature, 334:631–633 (1988).
McCarty, D.R., et al., Cell, 66:895–905 (1991).
Guarente, L., Trends Biochem. Sci., 20:517–521 (1995).
Horiuchi, J. et al., Mol. Cell Biol., 15:1203–1209 (1995).
Wolffe, A.P., Trends Biochem, Sci., 19:240–244 (1994). (Abstract).
Brownell, J.E. et al., Cell, 84:843–851 (1996).
Perrey et al. "Molecular cloning of a lupin–specific gene from a cDNA library of suspension–cultured cells of Lupinus polyphyllus" Plant Molecular Biology, vol. 15, pp. 175–176 1990.
Yamaguchi–Shinozaki, et al., The Plant Cell 6:251–264 (1994).
Baker, S.S., et al., Plant Mol. Biol. 24:701–713 (1994).
Jiang, C., et al., Plant Mol. Biol. 30:679–684 (1996).
Horvath, D.P., et al., Plant Physiol 103:1047–1053 (1993).
Wang, H., et al., Plant Mol. Biol 28:605–617 (1995).
Okme–Takagi, M., et al., The Plant Cell 7:173–182 (1995).
Klucher, K.M., et al., The Plant Cell 8:659–671 (1996).
Wilson, K., et al., The Plant Cell 8:659–671 (1996).
Li, J.J. and I Herskowitz, Science 262:1870–1874 (1993).
Jofuku, K.D., et al., The Plant Cell 6:1211–1225 (1994).
Elliot, R.C., et al., The Plant Cell 8:155–168 (1996).
Weigel, D., The Plant Cell 7:388–389 (1995).
Choi, S.Y., et al., Plant Physiol. 108:849 (1995).

*Primary Examiner*—Ardin H. Marschel
*Assistant Examiner*—Jezia Riley
*Attorney, Agent, or Firm*—Wilson Sonsini Goodrich & Rosati

[57] ABSTRACT

A gene, designated as CBF1, encoding a protein, CBF1, which binds to a region regulating expression of genes which promote cold temperature and dehydration tolerance in plants is described. CBF1 is used to transform microorganisms and can be used to transform plants.

49 Claims, 7 Drawing Sheets

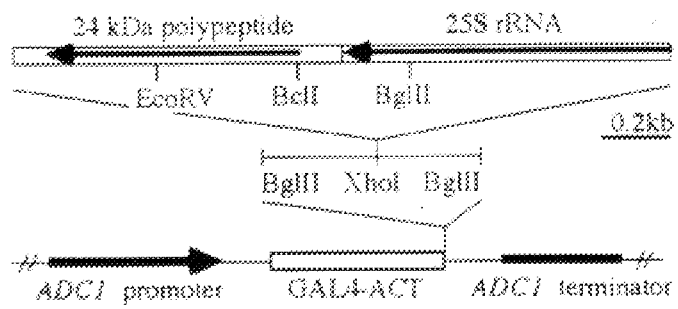
FIGURE 2A
FIGURE 2B
FIGURE 2C
NLS    AP2 Domain    Acidic Region
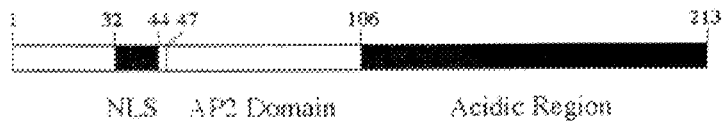
FIGURE 2D

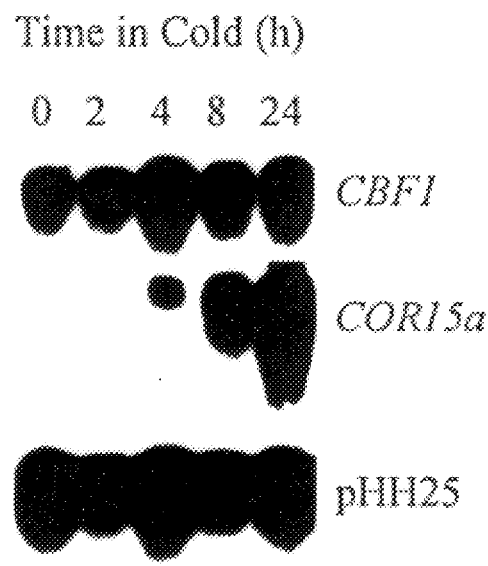
FIGURE 7A
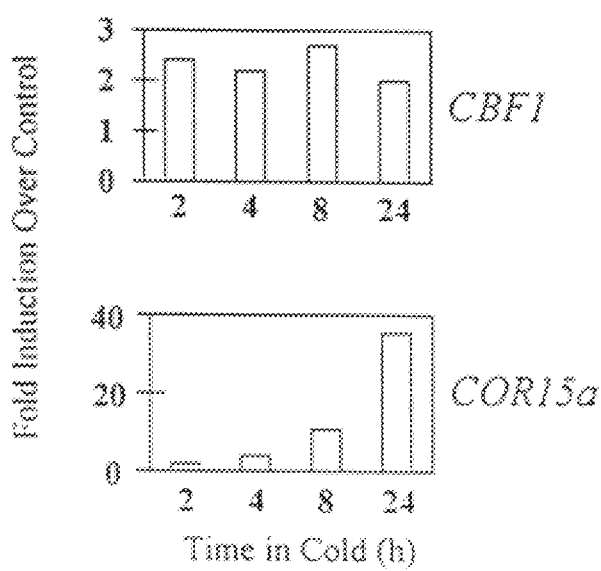
FIGURE 7B
FIGURE 7C

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 905
        ( B ) TYPE: Nucleic Acid
        ( C ) STRANDEDNESS: Single
        ( D ) TOPOLOGY: Linear ( i i ) MOLECULE TYPE: DNA ( i i i ) HYPOTHETICAL: No ( i v ) ANTI-SENSE: No ( v ) FRAGMENT TYPE:

( v i ) ORIGINAL SOURCE:
 ( A ) ORGANISM: Arabidopsis thaliana
 ( B ) STRAIN:
 ( C ) INDIVIDUAL ISOLATE: N/A
 ( D ) DEVELOPMENTAL STAGE: N/A
 ( E ) HAPLOTYPE: N/A
 ( F ) TISSUE TYPE: N/A
 ( G ) CELL TYPE: N/A
 ( H ) CELL LINE: N/A
 ( I ) ORGANELLE: N/A ( v i i ) IMMEDIATE SOURCE: N/A ( v i i i ) POSITION IN GENOME: N/A ( i x ) FEATURE:
 ( A ) NAME/KEY: CBF1 gene
 ( B ) LOCATION:
 ( C ) IDENTIFICATION METHOD: sequencing
 ( D ) OTHER INFORMATION:

( x ) PUBLICATION INFORMATION:

( x i ) SEQUENCE DESCRIPTION: SEQ ID NO:1:

```
AAAAAGAATC TACCTGAAAA GAAAAAAAAG AGAGAGAGAT ATAAATAGCT      50
TACCAAGACA GATATACTAT CTTTTATTAA TCCAAAAAGA CTGAGAACTC     100
TAGTAACTAC GTACTACTTA AACCTTATCC AGTTTCTTGA AACAGAGTAC     150
TCTGATCAAT GAACTCATTT TCAGCTTTTT CTGAAATGTT TGGCTCCGAT     200
TACGAGCCTC AAGGCGGAGA TTATTGTCCG ACGTTGGCCA CGAGTTGTCC     250
GAAGAAACCG GCGGGCCGTA AGAAGTTTCG TGAGACTCGT CACCCAATTT     300
ACAGAGGAGT TCGTCAAAGA AACTCCGGTA AGTGGGTTTC TGAAGTGAGA     350
GAGCCAAACA AGAAAACCAG GATTTGGCTC GGGACTTTCC AAACCGCTGA     400
GATGGCAGCT CGTGCTCACG ACGTCGCTGC ATTAGCCCTC CGTGGCCGAT     450
CAGCATGTCT CAACTTCGCT GACTCGGCTT GGCGGCTACG AATCCCGGAG     500
TCAACATGCG CCAAGGATAT CCAAAAAGCG GCTGCTGAAG CGGCGTTGGC     550
TTTTCAAGAT GAGACGTGTG ATACGACGAC CACGGATCAT GGCCTGGACA     600
TGGAGGAGAC GATGGTGGAA GCTATTTATA CACCGGAACA GAGCGAAGGT     650
GCGTTTTATA TGGATGAGGA GACAATGTTT GGGATGCCGA CTTTGTTGGA     700
TAATATGGCT GAAGGCATGC TTTTACCGCC GCCGTCTGTT CAATGGAATC     750
ATAATTATGA CGGCGAAGGA GATGGTGACG TGTCGCTTTG GAGTTACTAA     800
TATTCGATAG TCGTTTCCAT TTTTGTACTA TAGTTTGAAA ATATTCTAGT     850
TCCTTTTTTA GAATGGTTCC TTCATTTTAT TTTATTTTAT TGTTGTAGAA     900
ACGAG                                                      905
```

( 2 ) INFORMATION FOR SEQ ID NO:2:

( i ) SEQUENCE CHARACTERISTICS:
  ( A ) LENGTH: 213
  ( B ) TYPE: Amino Acid
  ( C ) STRANDEDNESS: Single
  ( D ) TOPOLOGY: Linear ( i i ) MOLECULE TYPE: protein ( i i i ) HYPOTHETICAL: No ( i v ) ANTI-SENSE: No (v) FRAGMENT TYPE:

(vi) ORIGINAL SOURCE:
    (A) ORGANISM: Arabidopsis thaliana
    (B) STRAIN:
    (C) INDIVIDUAL ISOLATE: N/A
    (D) DEVELOPMENTAL STAGE: N/A
    (E) HAPLOTYPE: N/A
    (F) TISSUE TYPE: N/A
    (G) CELL TYPE: N/A
    (H) CELL LINE: N/A
    (I) ORGANELLE: N/A (vii) IMMEDIATE SOURCE: N/A (viii) POSITION IN GENOME: N/A (ix) FEATURE:
    (A) NAME/KEY: CBF1 protein
    (B) LOCATION:
    (C) IDENTIFICATION METHOD: sequencing
    (D) OTHER INFORMATION:

(x) PUBLICATION INFORMATION:

(xi) SEQUENCE DESCRIPTION: SEQ ID NO:2:

```
                Met Asn Ser Phe Ser Ala Phe Ser Glu Met Phe Gly Ser Asp
                                  5                  10
Tyr Glu Pro Gln Gly Gly Asp Tyr Cys Pro Thr Leu Ala Thr Ser Cys Pro Lys
 15              20                  25                  30
Lys Pro Ala Gly Arg Lys Lys Phe Arg Glu Thr Arg His Pro Ile Tyr Arg Gly
         35                  40                  45                  50
Val Arg Gln Arg Asn Ser Gly Lys Trp Val Ser Glu Val Arg Glu Pro Asn Lys
                 55                  60                  65
Lys Thr Arg Ile Trp Leu Gly Thr Phe Gln Thr Ala Glu Met Ala Ala Arg Ala
     70                  75                  80                  85
His Asp Val Ala Ala Leu Ala Leu Arg Gly Arg Ser Ala Cys Leu Asn Phe Ala
             90                  95                 100
Asp Ser Ala Trp Arg Leu Arg Ile Pro Glu Ser Thr Cys Ala Lys Asp Ile Gln
105                 110                 115                 120
Lys Ala Ala Ala Glu Ala Ala Leu Ala Phe Gln Asp Glu Thr Cys Asp Thr Thr
        125                 130                 135                 140
Thr Thr Asp His Gly Leu Asp Met Glu Thr Met Val Glu Ala Ile Tyr Thr
                145                 150                 155
Pro Glu Gln Ser Glu Gly Ala Phe Tyr Met Asp Glu Glu Thr Met Phe Gly Met
        160                 165                 170                 175
Pro Thr Leu Leu Asp Asn Met Ala Glu Gly Met Leu Leu Pro Pro Pro Ser Val
                180                 185                 190
Gln Trp Asn His Asn Tyr Asp Gly Glu Gly Asp Gly Asp Val Ser Leu Trp Ser
195                 200                 205                 210
Tyr
```

(2) INFORMATION FOR SEQ ID NO:3:

(i) SEQUENCE CHARACTERISTICS:
        (A) LENGTH: 27
        (B) TYPE: Nucleic Acid
        (C) STRANDEDNESS: Single
        (D) TOPOLOGY: Linear (ii) MOLECULE TYPE: DNA (iii) HYPOTHETICAL: No (iv) ANTI-SENSE: No -continued

```
          ( v ) FRAGMENT TYPE:

( v i ) ORIGINAL SOURCE:
                    ( A ) ORGANISM: N/A - Synthetic
                    ( B ) STRAIN:
                    ( C ) INDIVIDUAL ISOLATE: N/A
                    ( D ) DEVELOPMENTAL STAGE: N/A
                    ( E ) HAPLOTYPE: N/A
                    ( F ) TISSUE TYPE: N/A
                    ( G ) CELL TYPE: N/A
                    ( H ) CELL LINE: N/A
                    ( I ) ORGANELLE: N/A ( v i i ) IMMEDIATE SOURCE: N/A ( v i i i ) POSITION IN GENOME: N/A ( i x ) FEATURE:
                    ( A ) NAME/KEY:
                    ( B ) LOCATION:
                    ( C ) IDENTIFICATION METHOD: sequencing
                    ( D ) OTHER INFORMATION: Table 1

( x ) PUBLICATION INFORMATION:

( x i ) SEQUENCE DESCRIPTION: SEQ ID NO:3:

G A T C A T T T C A    T G G C C G A C C T    G C T T T T T                                                  2 7

( 2 ) INFORMATION FOR SEQ ID NO:4:

( i ) SEQUENCE CHARACTERISTICS:
                    ( A ) LENGTH: 28
                    ( B ) TYPE: Nucleic Acid
                    ( C ) STRANDEDNESS: Single
                    ( D ) TOPOLOGY: Linear ( i i ) MOLECULE TYPE: DNA ( i i i ) HYPOTHETICAL: No ( i v ) ANTI-SENSE: No ( v ) FRAGMENT TYPE:

( v i ) ORIGINAL SOURCE:
                    ( A ) ORGANISM: N/A - Synthetic
                    ( B ) STRAIN:
                    ( C ) INDIVIDUAL ISOLATE: N/A
                    ( D ) DEVELOPMENTAL STAGE: N/A
                    ( E ) HAPLOTYPE: N/A
                    ( F ) TISSUE TYPE: N/A
                    ( G ) CELL TYPE: N/A
                    ( H ) CELL LINE: N/A
                    ( I ) ORGANELLE: N/A ( v i i ) IMMEDIATE SOURCE: N/A ( v i i i ) POSITION IN GENOME: N/A ( i x ) FEATURE:
                    ( A ) NAME/KEY:
                    ( B ) LOCATION:
                    ( C ) IDENTIFICATION METHOD: sequencing
                    ( D ) OTHER INFORMATION: Table 1

( x ) PUBLICATION INFORMATION:

( x i ) SEQUENCE DESCRIPTION: SEQ ID NO:4:

C A C A A T T T C A    A G A A T T C A C T    G C T T T T T T                                                  2 8

( 2 ) INFORMATION FOR SEQ ID NO:5:

( i ) SEQUENCE CHARACTERISTICS:
                    ( A ) LENGTH: 27
                    ( B ) TYPE: Nucleic Acid
```

( C ) STRANDEDNESS: Single
( D ) TOPOLOGY: Linear ( i i ) MOLECULE TYPE: DNA ( i i i ) HYPOTHETICAL: No ( i v ) ANTI-SENSE: No ( v ) FRAGMENT TYPE:

( v i ) ORIGINAL SOURCE:
( A ) ORGANISM: N/A - Synthetic
( B ) STRAIN:
( C ) INDIVIDUAL ISOLATE: N/A
( D ) DEVELOPMENTAL STAGE: N/A
( E ) HAPLOTYPE: N/A
( F ) TISSUE TYPE: N/A
( G ) CELL TYPE: N/A
( H ) CELL LINE: N/A
( I ) ORGANELLE: N/A ( v i i ) IMMEDIATE SOURCE: N/A ( v i i i ) POSITION IN GENOME: N/A ( i x ) FEATURE:
( A ) NAME/KEY:
( B ) LOCATION:
( C ) IDENTIFICATION METHOD: sequencing
( D ) OTHER INFORMATION: Table 1

( x ) PUBLICATION INFORMATION:

( x i ) SEQUENCE DESCRIPTION: SEQ ID NO:5:

GATCATTTCA TGGTATGTCT GCTTTTT                    27

( 2 ) INFORMATION FOR SEQ ID NO:6:

( i ) SEQUENCE CHARACTERISTICS:
( A ) LENGTH: 27
( B ) TYPE: Nucleic Acid
( C ) STRANDEDNESS: Single
( D ) TOPOLOGY: Linear ( i i ) MOLECULE TYPE: DNA ( i i i ) HYPOTHETICAL: No ( i v ) ANTI-SENSE: No ( v ) FRAGMENT TYPE:

( v i ) ORIGINAL SOURCE:
( A ) ORGANISM: N/A - Synthetic
( B ) STRAIN:
( C ) INDIVIDUAL ISOLATE: N/A
( D ) DEVELOPMENTAL STAGE: N/A
( E ) HAPLOTYPE: N/A
( F ) TISSUE TYPE: N/A
( G ) CELL TYPE: N/A
( H ) CELL LINE: N/A
( I ) ORGANELLE: N/A ( v i i ) IMMEDIATE SOURCE: N/A ( v i i i ) POSITION IN GENOME: N/A ( i x ) FEATURE:
( A ) NAME/KEY:
( B ) LOCATION:
( C ) IDENTIFICATION METHOD: sequencing
( D ) OTHER INFORMATION: Table 1

( x ) PUBLICATION INFORMATION:

( x i ) SEQUENCE DESCRIPTION: SEQ ID NO:6:

GATCATTTCA TGGAATCACT GCTTTTT                                                                                                  27

( 2 ) INFORMATION FOR SEQ ID NO:7:

( i ) SEQUENCE CHARACTERISTICS:
          ( A ) LENGTH: 27
          ( B ) TYPE: Nucleic Acid
          ( C ) STRANDEDNESS: Single
          ( D ) TOPOLOGY: Linear ( i i ) MOLECULE TYPE: DNA ( i i i ) HYPOTHETICAL: No ( i v ) ANTI-SENSE: No ( v ) FRAGMENT TYPE:

( v i ) ORIGINAL SOURCE:
          ( A ) ORGANISM: N/A - Synthetic
          ( B ) STRAIN:
          ( C ) INDIVIDUAL ISOLATE: N/A
          ( D ) DEVELOPMENTAL STAGE: N/A
          ( E ) HAPLOTYPE: N/A
          ( F ) TISSUE TYPE: N/A
          ( G ) CELL TYPE: N/A
          ( H ) CELL LINE: N/A
          ( I ) ORGANELLE: N/A ( v i i ) IMMEDIATE SOURCE: N/A ( v i i i ) POSITION IN GENOME: N/A ( i x ) FEATURE:
          ( A ) NAME/KEY:
          ( B ) LOCATION:
          ( C ) IDENTIFICATION METHOD: sequencing
          ( D ) OTHER INFORMATION: Table 1

( x ) PUBLICATION INFORMATION:

( x i ) SEQUENCE DESCRIPTION: SEQ ID NO:7:

GATCACTTGA TGGCCGACCT CTTTTTT                                                                                                  27

( 2 ) INFORMATION FOR SEQ ID NO:8:

( i ) SEQUENCE CHARACTERISTICS:
          ( A ) LENGTH: 27
          ( B ) TYPE: Nucleic Acid
          ( C ) STRANDEDNESS: Single
          ( D ) TOPOLOGY: Linear ( i i ) MOLECULE TYPE: DNA ( i i i ) HYPOTHETICAL: No ( i v ) ANTI-SENSE: No ( v ) FRAGMENT TYPE:

( v i ) ORIGINAL SOURCE:
          ( A ) ORGANISM: N/A - Synthetic
          ( B ) STRAIN:
          ( C ) INDIVIDUAL ISOLATE: N/A
          ( D ) DEVELOPMENTAL STAGE: N/A
          ( E ) HAPLOTYPE: N/A
          ( F ) TISSUE TYPE: N/A
          ( G ) CELL TYPE: N/A
          ( H ) CELL LINE: N/A
          ( I ) ORGANELLE: N/A ( v i i ) IMMEDIATE SOURCE: N/A ( v i i i ) POSITION IN GENOME: N/A ( i x ) FEATURE:
          ( A ) NAME/KEY:

(B) LOCATION:
(C) IDENTIFICATION METHOD: sequencing
(D) OTHER INFORMATION: Table 1

(x) PUBLICATION INFORMATION:

(xi) SEQUENCE DESCRIPTION: SEQ ID NO:8:

GATCAATATA CTACCGACAT GAGTTCT 27

(2) INFORMATION FOR SEQ ID NO:9:

(i) SEQUENCE CHARACTERISTICS:
(A) LENGTH: 25
(B) TYPE: Nucleic Acid
(C) STRANDEDNESS: Single
(D) TOPOLOGY: Linear (ii) MOLECULE TYPE: DNA (iii) HYPOTHETICAL: No (iv) ANTI-SENSE: No (v) FRAGMENT TYPE:

(vi) ORIGINAL SOURCE:
(A) ORGANISM: N/A - Synthetic
(B) STRAIN:
(C) INDIVIDUAL ISOLATE: N/A
(D) DEVELOPMENTAL STAGE: N/A
(E) HAPLOTYPE: N/A
(F) TISSUE TYPE: N/A
(G) CELL TYPE: N/A
(H) CELL LINE: N/A
(I) ORGANELLE: N/A (vii) IMMEDIATE SOURCE: N/A (viii) POSITION IN GENOME: N/A (ix) FEATURE:
(A) NAME/KEY:
(B) LOCATION:
(C) IDENTIFICATION METHOD: sequencing
(D) OTHER INFORMATION: Table 1

(x) PUBLICATION INFORMATION:

(xi) SEQUENCE DESCRIPTION: SEQ ID NO:9:

ACTACCGACA TGAGTTCCAA AAAGC 25

(2) INFORMATION FOR SEQ ID NO:10:

(i) SEQUENCE CHARACTERISTICS:
(A) LENGTH: 60
(B) TYPE: Amino Acid
(C) STRANDEDNESS: Single
(D) TOPOLOGY: Linear (ii) MOLECULE TYPE: Polypeptide (iii) HYPOTHETICAL: No (iv) ANTI-SENSE: No (v) FRAGMENT TYPE:

(vi) ORIGINAL SOURCE:
(A) ORGANISM: Arabidopsis thaliana
(B) STRAIN:
(C) INDIVIDUAL ISOLATE: N/A
(D) DEVELOPMENTAL STAGE: N/A
(E) HAPLOTYPE: N/A
(F) TISSUE TYPE: N/A
(G) CELL TYPE: N/A
(H) CELL LINE: N/A (I) ORGANELLE: N/A (vii) IMMEDIATE SOURCE: N/A (viii) POSITION IN GENOME: N/A (ix) FEATURE:
    (A) NAME/KEY:
    (B) LOCATION:
    (C) IDENTIFICATION METHOD: sequencing
    (D) OTHER INFORMATION: Figure 2D (x) PUBLICATION INFORMATION:

(xi) SEQUENCE DESCRIPTION: SEQ ID NO:10:

```
Ile Tyr Arg Gly Val Arg Gln Arg Asn Ser Gly Lys
                  5                   10

Trp Val Ser Glu Val Arg Glu Pro Asn Lys Lys Thr
             15                  20

Arg Ile Trp Leu Gly Thr Phe Gln Thr Ala Glu Met
 25                  30                   35

Ala Ala Arg Ala His Asp Val Ala Ala Leu Ala Leu
             40                  45

Arg Gly Arg Ser Ala Cys Leu Asn Phe Ala Asp Ser
 50                   55                       60
```

(2) INFORMATION FOR SEQ ID NO:11:

(i) SEQUENCE CHARACTERISTICS:
        (A) LENGTH: 61
        (B) TYPE: Amino Acid
        (C) STRANDEDNESS: Single
        (D) TOPOLOGY: Linear (ii) MOLECULE TYPE: Polypeptide (iii) HYPOTHETICAL: No (iv) ANTI-SENSE: No (v) FRAGMENT TYPE:

(vi) ORIGINAL SOURCE:
        (A) ORGANISM: Tobacco
        (B) STRAIN:
        (C) INDIVIDUAL ISOLATE: N/A
        (D) DEVELOPMENTAL STAGE: N/A
        (E) HAPLOTYPE: N/A
        (F) TISSUE TYPE: N/A
        (G) CELL TYPE: N/A
        (H) CELL LINE: N/A
        (I) ORGANELLE: N/A (vii) IMMEDIATE SOURCE: N/A (viii) POSITION IN GENOME: N/A (ix) FEATURE:
    (A) NAME/KEY:
    (B) LOCATION:
    (C) IDENTIFICATION METHOD: sequencing
    (D) OTHER INFORMATION: Figure 2D (x) PUBLICATION INFORMATION:

(xi) SEQUENCE DESCRIPTION: SEQ ID NO:11:

```
His Tyr Arg Gly Val Arg Gln Arg Pro Trp Gly Lys
                  5                   10

Phe Ala Ala Glu Ile Arg Asp Pro Ala Lys Asn Gly
             15                  20

Ala Arg Val Trp Leu Gly Thr Tyr Glu Thr Ala Glu
```

```
              25                           30                           35
Glu  Ala  Ala  Leu  Ala  Tyr  Asp  Lys  Ala  Ala  Tyr  Arg
                   40                          45

Met  Arg  Gly  Ser  Lys  Ala  Leu  Leu  Asn  Phe  Pro  His
         50                     55                      60

Arg
```

DNA AND ENCODED PROTEIN WHICH REGULATES COLD AND DEHYDRATION REGULATED GENES

BACKGROUND OF THE INVENTION (1) Summary of the Invention

The present invention relates to a gene, CBF1, encoding a protein, designated as CBF1, which binds to a region regulating expression of genes which are activated during acclimation to cold temperature and drought. The gene is expressed in microorganisms and can be used to produce recombinant plants.

(2) Description of Related Art

Environmental factors serve as cues to trigger a number of specific changes in plant growth and development. One such factor is low temperature. Prominent examples of cold-regulated processes include cold acclimation, the increase in freezing tolerance that occurs in response to low non-freezing temperatures (Guy, C. L., Annu. Rev. Plant Physiol. Plant Mol. Biol. 41:187–223 (1990)); vernalization, the shortening of time to flowering induced by low temperature (Lang, A., in Encyclopedia of Plant Physiology, Vol. 15-1, ed. Ruhland, W. (Springer, Berlin), pp. 1489–1536 (1965)); and stratification, the breaking of seed dormancy by low temperature (Berry, J. A. and J. K. Raison, in Encyclopedia of Plant Physiology, Vol. 12A, eds. Lange, O. L., Nobel, P. S., Osmond, C. B. and Ziegler, H. (Springer, Berlin), pp. 277–338 (1981)). Due to the fundamental nature and agronomic importance of these processes, there is interest in understanding how plants sense and respond to low temperature. One approach being taken is to determine the signal transduction pathways and regulatory mechanisms involved in cold-regulated gene expression.

Strong evidence exists for calcium having a role in low temperature signal transduction and regulation of at least some COR (cold-regulated) genes. Dhindsa and colleagues (Monroy, A. F., et al, Plant Physiol. 102:1227–1235 (1993); Monroy, A. F., and R. S., The Plant Cell, 7:321–331 (1995)) have shown that, in alfalfa, calcium chelators and calcium channel blockers prevent low temperature induction of COR genes and that calcium ionophores and calcium channel agonists induce expression of COR genes at normal growth temperatures. Similarly, Knight et al (The Plant Cell 8:489–503 (1996)) have shown that cold-induced expression of the Arabidopsis thaliana COR gene KIN1 is inhibited by calcium chelators and calcium channel blockers. These results suggest that low temperature triggers an influx of extracellular calcium that activates a signal transduction pathway that induces the expression of COR genes. Consistent with this notion is the finding that low temperature evokes transient increases in cytosolic calcium levels in plants (Knight, M. R. et al, Nature 352:524–526 (1991); Knight, H., et al., The Plant Cell 8:489–503 (1996)). In addition, low temperatures have been shown to stimulate the activity of mechanosensitive calcium-selective cation channels in plants (Ding, J. P. and B. G. Pickard, Plant J. 3:713–720 (1993)).

Recent efforts have led to the identification of a cis-acting cold-regulatory element in plants, the C-repeat/DRE (Yamaguchi-Shinozaki, et al., The Plant Cell 6:251–264 (1994); Baker, S. S., et al., Plant. Mol. Biol. 24:701–713 (1994); Jiang, C., et al., Plant Mol. Biol. 30:679–684 (1996)). The element, which has a 5 base pair core sequence for CCGAC, is present once to multiple times in all plant cold-regulated promoters that have been described to date; these include the promoters of the COR15a (Baker, S. S., et al, Plant. Mol. Biol. 24:701–713 (1994)), COR78/RD29A (Horvath, D. P., et al, Plant Physiol. 103:1047–1053 (1993); Yamaguchi-Shinozaki, K., et al., The Plant Cell 6:251–264 (1994)), COR6.6 (Wang, H., et al., Plant Mol. biol. 28:605–617 (1995)) and KIN1 (Wang, H., et al, Plant Mol. Biol. 28:605–617 (1995)) genes of Arabidopsis and the BN115 gene of Brassica napus (White, T. C., et al, Plant Physiol. 106:917–928 (1994)). Deletion analysis of the Arabidopsis COR15a gene suggested that the CCGAC sequence, designated the C-repeat, might be part of a cis-acting cold-regulatory element (Baker, S. S., et al., Plant Mol. Biol. 24:701–713 (1994)). That this was the case was first demonstrated by Yamaguchi-Shinozaki and Shinozaki (Yamaguchi-Shinozaki, K., et al., The Plant Cell 6:251–264 (1994)) who showed that two of the C-repeat sequences present in the promoter of COR78/RD29A induced cold-regulated gene expression when fused to a reporter gene. It was also found that these two elements stimulate transcription in response to dehydration and high salinity and thus, was designated the DRE (dehydration, low temperature and high salt regulatory element). Interestingly, two other C-repeats present in the promoter of COR78/RD29A did not impart regulation in response to dehydration and high salt; whether they impart cold-regulated gene expression is not known. Recent studies by Jiang et al (Jiang, C., et al., Plant Mol. Biol. 30:679–684 (1996)) indicate that the C-repeats (referred to as low temperature response elements) present in the promoter of the B. napus BN115 gene also impart cold-regulated gene expression, but do not activate gene expression in response to dehydration.

U.S. Pat. Nos. 5,296,462 and 5,356,816 to Thomashow describe the genes encoding the proteins involved in cold regulation in Arabidopsis thaliana. In particular the DNA encoding the COR15 proteins is described. These proteins are significant in promoting cold tolerance in plants; however, the mode of activation is not described.

There is a need for a protein which regulates the expression of genes encoding cold and drought tolerance genes.

OBJECTS

Therefore, it is an object of the present invention to provide a protein and gene encoding the protein which regulates expression of genes activated during acclimation to cold temperature and dehydration stress. It is further an object of the present invention to provide a unique protein and DNA sequences encoding the protein. These and other objects will become increasingly apparent by reference to the following description and the drawings.

IN THE DRAWINGS

FIGS. 1A and 1B show how the yeast reporter strains were constructed. FIG. 1A is a schematic diagram showing the screening strategy. Yeast reporter strains were constructed that carried C-repeat/DRE sequences as UAS elements fused upstream of a lacZ reporter gene with a minimal GALL promoter. The strains were transformed with an Arabidopsis expression library that contained random cDNA inserts fused to the GAL4 activation domain (GAL4-ACT) and screened for blue colony formation on X-gal-treated filters. FIG. 1B is a chart showing activity of the "positive" cDNA clones in yeast reporter strains. The oligonucleotides (oligos) used to make the UAS elements, and their number and direction of insertion, are indicated by the arrows.

FIGS. 2A, 2B, 2C and 2D provide an analysis of the pACT-11 cDNA clone. FIG. 2A is a schematic drawing of the pACT-11 cDNA insert indicating the location and 5' to 3' orientation of the 24 kDa polypeptide and 25s rRNA sequences. The cDNA insert was cloned into the XhoI site of the pACT vector. FIG. 2B is a DNA and amino acid sequence of the 24 kDa polypeptide (SEQ ID NO:1 and SEQ ID NO:2). The AP2 domain is indicated by a double underline. The basic amino acids that potentially act as a nuclear localization signal are indicated with asterisks. The BclI site immediately upstream of the 24 kDa polypeptide used in subcloning the 24 kDa polypeptide and the EcoRV site used in subcloning the 3' end of CBF1 are indicated by single underlines. FIG. 2C is a schematic drawing indicating the relative positions of the potential nuclear localization signal (NLS), the AP2 domain and the acidic region of the 24 kDa polypeptide. Numbers indicate amino acid residues. FIG. 2D is a chart showing comparison of the AP2 domain of the 24 kDa polypeptide with that of the tobacco DNA binding protein EREBP2 (Okme-Takagi, M., et al., The Plant Cell 7:173–182 (1995) SEQ ID NOS: 10 and 11). Identical amino acids are indicated with single lines; similar amino acids are indicated by double dots; amino acids that are invariant in AP2 domains are indicated with asterisks (Klucher, K. M., et al., The Plant Cell 8:137–153 (1996)); and the histidine residues present in CBF1 and TINY (Wilson, K., et al., The Plant Cell 8:659–671 (1996)) that are tyrosine residues in all other described AP2 domains are indicated with a caret. A single amino acid gap in the CBF1 sequence is indicated by a single dot.

FIG. 3 is a chart showing activation of reporter genes by the 24 kDa polypeptide. Restriction fragments of pACT-11 carrying the 24 kDa polypeptide (BclI-BglII) or the 24 kDa polypeptide plus a small amount of 25s RNA sequence (BglII—BglII) were inserted in both orientations into the yeast expression vector pDB20.1 (see FIG. 2A and 2B for location of BclI and BglII restriction sites). These "expression constructs" were transformed into yeast strains carrying the lacZ reporter gene fused to direct repeat dimers of either the wild-type COR15a C-repeat/DRE (oligonucleotide MT50) or the mutant M2COR15a C-repeat/DRE (oligonucleotide MT80). The specific activity of β-galactosidase (nmoles o-nitrophenol produced/min$^{-1}$×mg protein $^{-1}$) was determined from cultures grown in triplicate. Standard deviations are indicated. Abbreviations: pADC1, ADC1 promoter; tADC1, ADC1 terminator.

FIG. 4 is a photograph of an electrophoresis gel showing expression of the recombinant 24 kDa polypeptide in *E. coli*. Shown are the results of SDS-PAGE analysis of protein extracts prepared from *E. coli* harboring either the expression vector alone (vector) or the vector plus an insert encoding the 24 kDa polypeptide in sense (sense insert) or antisense (antisense insert) orientation. The 28 kDa fusion protein (see Materials and Methods) is indicated by an arrow.

FIG. 5 is a photograph of a gel for shift assays indicating that CBF1 binds to the C-repeat/DRE. The C-repeat/DRE probe (1 ng) used in all reactions was a $^{32}$P-labeled dimer of the oligonucleotide MT50 (wild type C-repeat/DRE from COR15a). The protein extracts used in the first four lanes were either bovine serum albumin (BSA) or the indicated CBF1 sense, antisense and vector extracts described in FIG. 4. The eight lanes on the right side of the figure used the CBF1 sense protein extract plus the indicated competitor C-repeat/DRE sequences (100 ng). The numbers 1X, 2X and 3X indicate whether the oligonucleotides were monomers, dimers or trimers, respectively, of the indicated C-repeat/DRE sequences.

FIG. 6 is a photograph of a southern blot analysis indicating CBF1 is a unique or low copy number gene. Arabidopsis DNA (~1 μg) was digested with the indicated restriction endonucleases and southern transfers were prepared and hybridized with a $^{32}$P-labeled probe encoding the entire CBF1 polypeptide.

FIGS. 7A, 7B and 7C relate to CBF1 transcripts in control and cold-treated Arabidopsis. FIG. 7A is a photograph of a membrane RNA isolated from Arabidopsis plants that were grown at 22° C. or grown at 22° C. and transferred to 2.5° C. for the indicated times. Northern transfers were prepared from either total RNA (10 μg) or poly(A)$^+$ RNA (1 μg) and hybridized with $^{32}$P-labeled probes for the entire CBF1 coding sequence or the cold-regulated COR15a gene, respectively. The membranes were stripped and re-probed with $^{32}$P-labeled pHH25, a cDNA encoding the small subunit of rubisco. The transcript levels for pHH25 are about the same in control and cold-treated plants (Hajela, R. K., et al., Plant Physiol. 93:1246–1252 (1990)). FIGS. 7B and 7C are graphs showing relative transcript levels of CBF1 and COR15a in control and cold-treated plants. The radioactivity present in the samples described in FIG. 7A were quantified using a Betascope 603 blot analyzer and plotted as relative transcript levels (the values for the 22° C. grown plants being arbitrarily set as 1) after adjusting for differences in loading using the values obtained with the pHH25 probe.

DESCRIPTION OF PREFERRED EMBODIMENTS

Figures 1A, 1B:
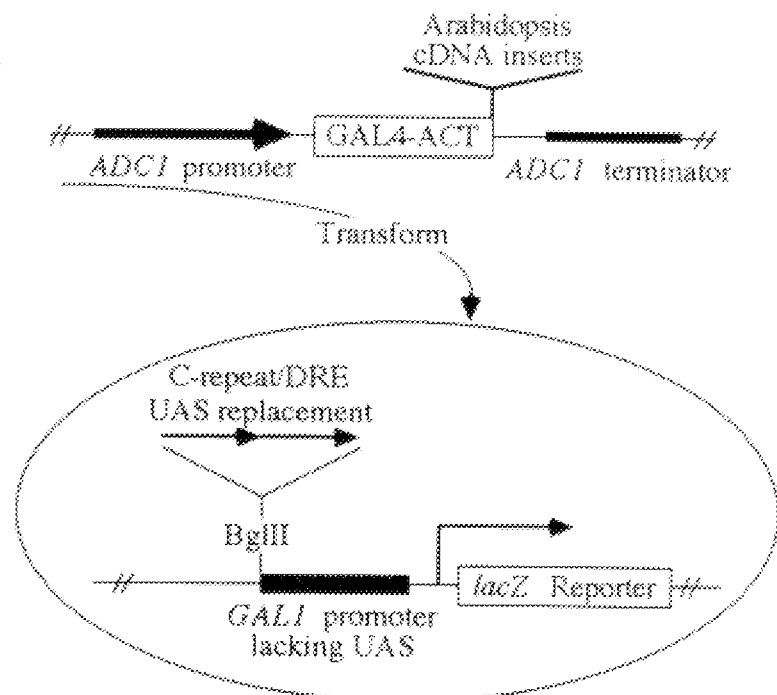

The present invention relates to an isolated DNA encoding a protein having a sequence of amino acids essentially homologous to that set forth in SEQ ID NO:2 such that upon providing the DNA encoding the protein in a living plant material a transcription regulating region controlling at least one cold or dehydration regulated gene in the plant material is activated.

The present invention also relates to a plasmid deposited as ATCC 98063 containing a DNA insert encoding a protein which activates a transcription regulating region identified as the C-repeat/DRE.

The present invention also relates to a plasmid containing a DNA insert encoding a protein comprising a sequence of amino acids essentially homologous to that set forth in SEQ ID NO:2 such that upon providing the DNA encoding protein in a living plant material a transcription regulating region controlling at least one cold or dehydration regulated gene in the plant material is activated.

The present invention also relates to a microorganism containing a plasmid having a DNA insert encoding a protein comprising a sequence of amino acids essentially homologous to that set forth in SEQ ID NO:1 such that upon providing the DNA in a living plant material a transcription regulating region controlling at least one cold or dehydration regulated gene in the living plant material is activated.

The present invention also relates to a plant material containing a recombinant DNA encoding a protein comprising a sequence of amino acids essentially homologous to that set forth in SEQ ID NO:1 such that a transcription regulating region controlling at least one cold or dehydration regulated gene in the plant material is activated by the protein.

The present invention also relates to a protein free of other proteins comprising a sequence of amino acids essentially homologous to that set forth in SEQ ID NO:2 such that upon providing DNA encoding the protein in a living plant material a transcription regulating region controlling at least one cold or dehydration regulated gene in the plant material is activated.

The present invention also relates to a protein free of other proteins having an amino acid sequence as set forth in SEQ ID NO:2.

The present invention also relates to a protein free of other proteins of *Arabidopsis thaliana* having a molecular weight of about 24 kD as measured in an electrophoresis gel, which binds to a transcription regulating DNA region controlling a cold or dehydration regulated gene of the *Arabidopsis thaliana*.

The present invention also relates to a protein as encoded by a DNA in plasmid pEJS251 deposited as ATCC 98063.

The present invention also relates to a composition useful for introduction into plants to increase cold or dehydration tolerance of the plant which comprises:
 (a) a protein having a sequence of amino acids essentially homologous to that set forth in SEQ ID NO:2 such that upon providing the DNA encoding the protein in a living plant material a transcription regulating region controlling at least one cold or dehydration regulated gene in the plant material is activated; and
 (b) a carrier for the introduction of the protein into the plant.

The present invention relates to a composition useful for introduction into plants to increase cold or dehydration tolerance of the plant which comprises:
 (a) a protein as encoded by a DNA in a plasmid deposited as ATCC 98063; and
 (b) a carrier for the introduction of the protein into the plant.

The present invention relates to a method of regulating cold or dehydration tolerance of a living plant material which comprises:
 introducing into the living plant material a DNA encoding a protein comprising a sequence of amino acids essentially homologous to that set forth in SEQ ID NO:1 such that upon providing the DNA encoding the protein in the living plant material a transcription regulating region controlling at least one cold or dehydration regulated gene in the plant material is activated.

The term "cold" includes freezing temperatures as well as more elevated temperatures less than ambient temperatures. The term "dehydration" includes salt stress and osmotic stress.

Transformation means the process for changing the genotype of a recipient organism by the stable introduction of DNA by whatever means.

A transgenic plant is a plant which contains DNA sequences which were introduced by transformation. Horticultural and crop plants particularly benefit from the present invention.

Translation means the process whereby the genetic information in an mRNA molecule directs the order of specific amino acids during protein synthesis.

The term "essentially homologous" means that the DNA or protein is sufficiently duplicative of that set forth in FIG. 2B to produce the same result. Such DNA can be used as a probe to isolate DNA's in other plants.

A promoter is a DNA fragment which causes transcription of genetic material. For the purposes described herein, promoter is used to denote DNA fragments that permit transcription in plant cells.

A poly-A addition site is a nucleotide sequence which causes certain enzymes to cleave mRNA at a specific site and to add a sequence of adenylic acid residues to the 3'-end of the mRNA.

In the following description, the isolation of an *Arabidopsis thaliana* cDNA clone that encodes a C-repeat/DRE binding factor, CBF1 (C-repeat/DRE Binding Factor 1) is described. Expression of CBF1 in yeast activated transcription of reporter genes containing the C-repeat/DRE as an upstream activator sequence, but not mutant versions of the element, indicating that CBF1 is a transcription factor that binds to the C-repeat/DRE. Binding of CBF1 to the C-repeat/DRE was also demonstrated in gel shift assays using recombinant CBF1 protein expressed in *Escherichia coli*. Transcript levels of CBF1—which is a single or low copy number gene—increased only slightly (2 to 3 fold) in response to low temperature. Analysis of the deduced CBF1 amino acid sequence indicated that the protein has a potential nuclear localization sequence, a possible acidic activation domain and an AP2 domain, a DNA-binding motif of about 60 amino acids that is similar to those present in Arabidopsis proteins APETALA2, AINTEGUMENTA and TINY, the tobacco ethylene response element binding proteins, and numerous other plant proteins of unknown function. Implications of CBF1 activating transcription in yeast and possible mechanisms of regulating CBF1 activity in Arabidopsis are discussed.

*Escherichia coli* strain GM2163 containing plasmid pEJS251 was deposited under the Budapest Treaty on May 17, 1996 with the American Type Culture Collection, Rockville, Md. as ATCC 98063. All restrictions regarding access to the deposit will be lifted upon issuance and the term of the deposit is for at least 30 years after the deposit and at least 5 years after the most recent request and enforceable life patent.

EXAMPLE 1

Materials and Methods

Plant material and cold treatment. *A thaliana* (L.) Heyn. ecotype RLD plants were grown in pots in controlled environment chambers at 22° C. under constant illumination with cool-white fluorescent lamps (~100 $\mu$mol m$^{-2}$s$^{-1}$) essentially as described (Gilmour, S. J., Plant Physiol. 87:745–750 (1988)). Plants were cold-treated by placing pots in a cold room at 2.5° C. under constant illumination with cool-white florescent lamps (~25 $\mu$mol m$^{-2}$s$^{-1}$) for the indicated times.

Yeast reporter strains. Oligonucleotides (Table 1) (synthesized at the MSU Macromolecular Structure Facility) encoding either wild-type or mutant versions of the C-repeat/DRE were ligated into the BglII site of the lacZ reporter vector pBgl-lacZ (Li, J. J. and I. Herskowitz, Science 262:1870–1874 (1993); kindly provided by Joachim Li).

TABLE 1

Oligonucleotides encoding wild type and mutant versions of the C-repeat/DRE

| Oligonucleotide | C-repeat/DRE* | Sequence | SEQ ID NO: |
|---|---|---|---|
| MT50 | COR15a | gatcATTTCATGGCCGACCTGCTTTTT | 3 |
| MT52 | M1COR15a | CACAATTTCAaGaattcaCTGCTTTTTT | 4 |
| MT80 | M2COR15a | gatcATTTCATGGtatgtCTGCTTTTT | 5 |
| MT125 | M3COR15a | gatcATTTCATGGaatcaCTGCTTTTT | 6 |
| MT68 | COR15b | gatcACTTGATGGCCGACCTCTTTTTT | 7 |
| MT66 | COR78-1 | gatcAATATACTACCGACATGAGTTCT | 8 |
| MT86 | COR78-2 | ACTACCGACATGAGTTCCAAAAAGC | 9 |

*The C-repeat/DRE sequences tested are either wild-type found in the promoters of COR15a (Baker, S. S., et al., Plant. mol. Biol. 24:701–713 (1994)), COR15b or COR78/RD29A (Horvath, D. P., et al., Plant Physiol. 103: 1047–1053 (1993); Yamaguchi-shinozaki, K., et al., The Plant Cell 6:251–264 (1994)) or are mutant versions of the COR15a C-repeat/DRE (M1COR15a, M2COR15a and M3COR15a).
Uppercase letters designate bases in wild type C-repeat/DRE sequences. The core CCGAC sequence common to all C-repeats is indicated in bold type. Lowercase letters at the beginning of a sequence indicate bases added to facilitate cloning. The lowercase letters that are underlined indicate the mutations in the C-repeat/DRE sequence of COR15a.

The resulting reported constructs were integrated into the ura3 locus of *Saccharomyces cerevisiae* strain GGY1 (MATα Δgal4 Δgal80ura3 leu2 his3 ade2 tyr) (Li, J. J. and I. Herskowitz, Science 262:1870–1874 (1993); provided by Joachim Li) by transformation and selection for uracil prototrophy.

Screen of Arabidopsis cDNA library. The Arabidopsis pACT cDNA expression library that was constructed by John Walker and colleagues (NSF/DOE/USDA Collaborative Research in Plant Biology Program grant USDA 92-37105–7675) and deposited in the Arabidopsis Biological Resource Center (stock #CD4-10) was screened for clones encoding C-repeat/DRE binding domains. The cDNA library, harbored in *Escherichia coli* BNN132, was amplified by inoculating 0.5 ml of the provided glycerol stock into 1 L of M9 minimal glucose medium (Sambrook, J. et al, Molecular Cloning. A Laboratory Manual (Cold Spring Harbor Laboratory Press, Cold Spring Harbor, N.Y., 2nd Ed. (1989)) and shaking the bacteria for 20 h at 37° C. Plasmid DNA was isolated and purified by cesium chloride density gradient centrifugation (Sambrook et al (1989)) and transformed into the yeast GGY1 reporter strains selecting for leucine prototrophy. Yeast transformants that had been grown for 2 or 3 days at 30° C. were overlaid with either a nitrocellulose membrane filter (Schleicher and Schuell, Keene, N.H.) or Whatman #50 filter paper (Hillsboro, Oreg.) and incubated overnight at 30° C. The yeast impregnated filters were then lifted from the plate and treated with X-gal (5-bromo-4-chloro-3-indolyl β-D-galactosidase) to assay colonies for β-galactosidase activity (Li, J. J. and I. Herskowitz, Science 262:1870–1874 (1993)). Plasmid DNA from "positive" transformants (those forming blue colonies on the X-gal-treated filters) was recovered (Strathern, J. N., and D. R. Higgens, Methods Enzymol. 194:319–329 (1991)), propagated in *E. coli* DH5α and transformed back into the yeast reporter strains to confirm activity.

Yeast transformation and quantitative β-galactosidase assays. Yeast were transformed by either electroporation (Becker, D. M., et al., Methods Enzymol. 194:182–187 (1991)) or the lithium acetate/carrier DNA method (Schiestl, R. H., et al., Current Genetics 16:339–346 (1989)). Quantitative in vitro β-galactosidase assays were done as described (Rose, M., et al., Methods Enzymol. 101:167–180 (1983)).

Expression of CBF1 protein in *E. coli* and yeast. CBF1 was expressed in *E. coli* using the pET-28a(+) vector (Novagen, Madison, Wis.). The BglII-BclI restriction fragment of pACT-11 encoding CBF1 was ligated into the BamHI site of the vector bringing CBF1 under control of the T7 phage promoter. The construct resulted in a "histidine tag," a thrombin recognition sequence and a "T7 epitope tag" being fused to the amino terminus of CBF1. The construct was transformed into *E. coli* BL21 (DE3) and the recombinant CBF1 protein was expressed as recommended by the supplier (Novagen). Expression of CBF1 in yeast was accomplished by ligating restriction fragments encoding CBF1 (the BclI-BglII and BglII—BglII fragments from pACT-11) into the BglII site of pDB20.1 (Berger, S. L., et al., Cell 70:251–265 (1992); kindly provided by Steve Triezenberg) bringing CBF1 under control of the constitutive ADC1 (alcohol dehydrogenase constitutive 1) promoter.

Gel shift assays. Total soluble *E. coli* protein (40 ng) was incubated at room temperature in 10 μl of 1× binding buffer [15 mM HEPES (pH 7.9), 1 mM EDTA, 30mM KCl, 5% glycerol, 5BSA, 1 mM DTT) plus 50 ng poly(dI-dC):poly (dI-dC) (Pharmacia, Piscataway, N.J.) with or without 100 ng competitor DNA. After 10 min, probe DNA (1 ng) that was $^{32}$P-labeled by end-filling (Sambrook et al, 1989) was added and the mixture incubated for an additional 10 min. Samples were loaded onto polyacrylamide gels (4% w/v) and fractionated by electrophoresis at 150 V for 2 h (Sambrook et al). Probes and competitor DNAs were prepared from oligonucleotide inserts ligated into the BamHI site of pUC118 (Vieira, J., et al., Methods Enzymol. 153:3–11 (1987)). Orientation and concatenation number of the inserts were determined by dideoxy DNA sequence analysis (Sambrook, et al, (1989)). Inserts were recovered after restriction digestion with EcoRI and HindIII and fractionation on polyacrylamide gels (12% w/v) (Sambrook et al, 1989).

Northern and southern analysis. Total RNA was isolated from Arabidopsis (Gilmour, S. J., et al., Plant Physiol. 87:745–750 (1988)) and the poly(A)$^+$ fraction purified using oligo dT cellulose (Sambrook, et al (1989)). Northern transfers were prepared and hybridized as described (Hajela, R. K., et al., Plant physiol. 93:1246–1252 (1990)) except that high stringency wash conditions were at 50° C. in 0.1× SSPE [× SSPE is 3.6M NaCl, 20 mM EDTA, 0.2M Na$_2$-HPO$_4$ (pH7.7)], 0.5% SDS. Membranes were stripped in 0.1× SSPE, 0.5% SDS at 95° C. for 15 min prior to re-probing. Total Arabidopsis genomic DNA was isolated (Stockinger, E. J., et al., J. Heredity, 87:214–218 (1996)) and southern transfers prepared (Sambrook et al 1989) using nylon membranes (MSI, Westborough, Mass.). High stringency hybridization and wash conditions were as described by Walling et al (Walling, L. L., et al., Nucleic Acids Res. 16:10477–10492 (1988)). Low stringency hybridization was in 6× SSPE, 0.5% SDS, 0.25% low fat dried milk at 60° C. Low stringency washes were in 1× SSPE, 0.5% SDS at 50° C. Probes used for the entire CBF1 coding sequence and 3' end of CBF1 were the BclI/BglII and EcoRV/BglII restriction fragments from pACT-11, respectively, that had been gel purified (Sambrook et al (1989)). DNA probes were radiolabeled with $^{32}$P-nucleotides by random priming (Sambrook). Autoradiography was performed using hyperfilm-MP (Amersham, Arlington Heights, Ill.). Radioactivity was quantified using a Betascope 603 blot analyzer (Betagen Corp., Waltham, Mass.).

RESULTS

Screen for Arabidopsis cDNAs encoding a C-repeat/DRE binding domain. The "one-hybrid" strategy (Li, J. J. and I. Herskowitz, Science 262:1870–1874 (1993)) was used to screen for Arabidopsis CDNA clones encoding a C-repeat/ DRE binding domain. In brief, yeast strains were constructed that contained a lacZ reporter gene with either wild-type or mutant C-repeat/DRE sequences in place of the normal UAS (upstream activator sequence) of the GAL1 promoter (FIG. 1A). Yeast strains carrying these reporter constructs produced low levels of β-galactosidase and formed white colonies on filters containing X-gal. The reporter strains carrying the wild-type C-repeat/DRE sequences were transformed with a DNA expression library that contained random Arabidopsis cDNA inserts fused to the acidic activator domain of the yeast GAL4 transcription factor, "GAL4-ACT" (FIG. 1A). The notion was that some of the clones might contain a cDNA insert encoding a C-repeat/DRE binding domain fused to GLA4-ACT and that such a hybrid protein could potentially bind upstream of the lacZ reporter genes carrying the wild type C-repeat/DRE sequence, activate transcription of the lacZ gene and result in yeast forming blue colonies on X-gal-treated filters.

Upon screening about 2×10$^6$ yeast transformants, three "positive" cDNA clones were isolated; i.e., the clones caused yeast strains carrying lacZ reporters fused to wild-type C-repeat/DRE inserts to form blue colonies on X-gal-treated filters (FIG. 1B). The three cDNA clones did not cause a yeast strain carrying a mutant C-repeat/DRE fused to LacZ to turn blue (FIG. 1B). Thus, activation of the reporter genes by the cDNA clones appeared to be dependent on the C-repeat/DRE sequence. Restriction enzyme analysis and DNA sequencing indicated that the three cDNA clones had an identical 1.8 kb insert (FIG. 2A). One of the clones, designated pACT-11, was chosen for further study.

pACT-11 encodes a 24 kDa polypeptide with an AP2 domain. Our expectation was that the cDA insert in pACT-11 would have a C-repeat/DRE binding domain fused to the yeast GAL4-ACT sequence. However, DNA sequence analysis indicated that an open reading frame of only nine amino acids had been added to the C-terminus of GAL4-ACT. It seemed highly unlikely that such a short amino acid sequence could comprise a DNA binding domain. Also surprising was the fact that about half of the cDNA insert in pACT-11 corresponded to 25s rRNA sequences (FIG. 2A). Further analysis, however, indicated that the insert had an open reading frame, in opposite orientation to the GAL4-ACT sequence, deduced to encode a 24 kDa polypeptide (FIG. 2A–C). The polypeptide has a basic region that could potentially serve as a nuclear localization signal (Raikhel, N., Plant Physiol. 100:1627–1632 (1992)) and an acidic C-terminal half (pI of 3.6) that could potentially act as an acidic transcription activator domain (Hahn, S., Cell 72:481–483 (1993)). A Search of the nucleic acid and protein sequence databases indicated that there was no previously described homology of the 24 kDa polypeptide. However, the polypeptide did have an AP2 domain (Jofuku, K. D., et al., The Plant Cell 6:1211–1225 (1994)) (FIG. 2B, D), a DNA binding motif of about 60 amino acids (Ohme-Takagi, M., et al., The Plant Cell 7:173–182 (1994)) that is present in numerous plant proteins including the APETALA2 (Jofuku, K. D., et al., The Plant Cell 6:1211–1225 (1994)), AINTEGUMENTA (Klucher, K. M., et al., The Plant Cell 8:137–153 (1996); Elliot, R. C., et al., The Plant Cell 8:155–168 (1996)) and TINY (Wilson, K., et al., The Plant Cell 8:659–671 (1996)) proteins of Arabidopsis and the EREBPs (ethylene response element binding proteins) of tobacco (Ohme-Takagi, M., et al., The Plant Cell 7:173–182 (1995)).

Figure 3:
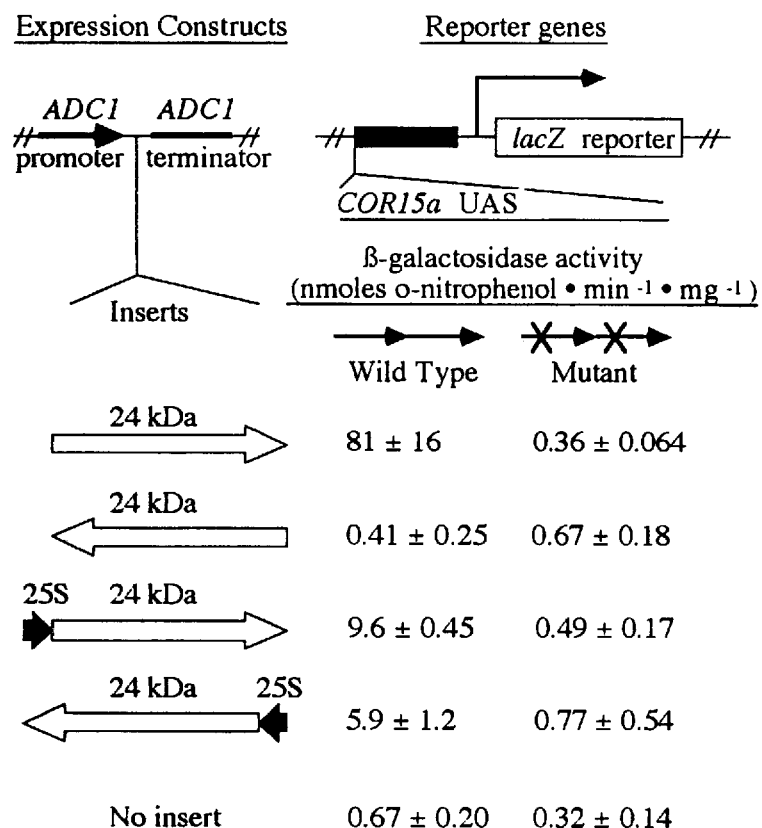

The 24 kDa polypeptide binds to the C-repeat/DRE and activates transcription in yeast. We hypothesized that the 24 kDa polypeptide was responsible for activating the lacZ reporter genes in yeast. To test this, the BclI-BglII fragment of pACT-11 containing the 24 kDa polypeptide, and the BglII-BglII fragment containing the 24 kDa polypeptide plus a small portion of the 25s rRNA sequence, was inserted into the yeast expression vector pDB20.1 (FIG. 3). Plasmids containing either insert in the same orientation as the ADC1 promoter stimulated synthesis of β-galactosidase when transformed into yeast strains carrying the lacZ reporter gene fused to a wild-type COR15a C-repeat/DRE (FIG. 3). The plasmids did not, however, stimulate synthesis of β-galactosidase when transformed into yeast strains carrying lacZ fused to a mutant version of the COR15a C-repeat/DRE (FIG. 3). These data indicated that the 24 kDa polypeptide could bind to the wild-type C-repeat/DRE and activate expression for the lacZ reporter gene in yeast. Additional experiments indicated that the 24 kDa polypeptide could activate expression of the lacZ reporter gene fused to either a wild-type COR78 C-repeat/DRE (dimer of MT66) or a wild-type COR15b C-repeat/DRE (dimer of MT 68) (not shown). A plasmid containing the BclI-BglII fragment (which encodes only the 24 kDa polypeptide) cloned in opposite orientation to the ADC1 promoter did not stimulate synthesis of β-galactosidase in reporter strains carrying the wild-type COR15a C-repeat/DRE fused to lacZ (FIG. 3). In contrast, a plasmid carrying the BglII—BglII fragment (containing the 24 kDa polypeptide plus some 25s rRNA sequences) cloned in opposite orientation to the ADC1 promoter produced significant levels of β-galactosidase in reporter strains carrying the wild-type COR15a C-repeat/ DRE (FIG. 3). Thus, a sequence located closely upstream of the 24 kDa polypeptide was able to serve as a cryptic promoter in yeast, a result that offered an explanation for how the 24 kDa polypeptide was expressed in the original pACT-11 clone.

Figure 4:
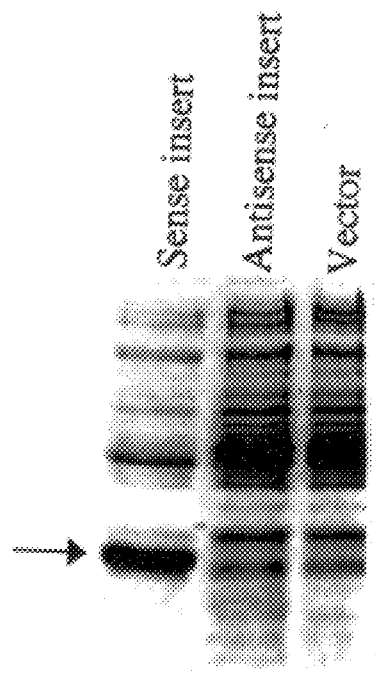
Figure 5:
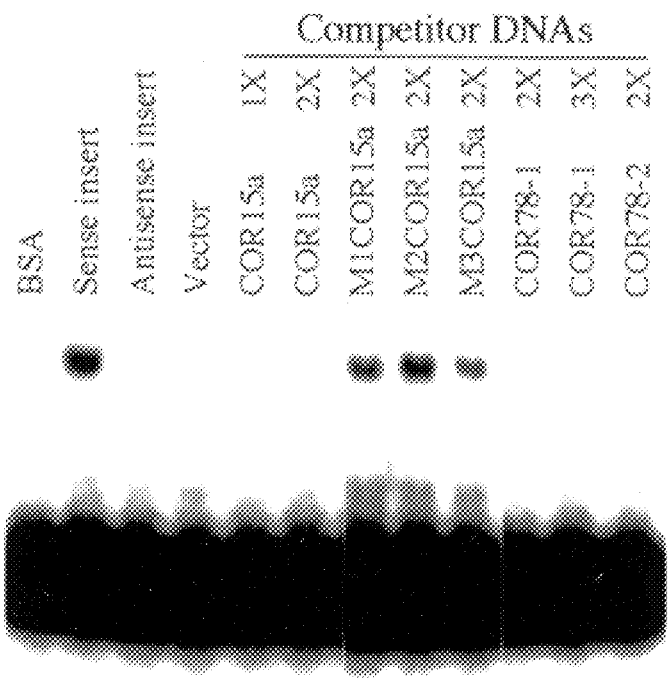

Gel shift analysis indicates that the 24 kDa polypeptide binds to the C-repeat/DRE. Gel shift experiments were conducted to demonstrate further that the 24 kDa polypeptide bound to the C-repeat/DRE. Specifically, the open reading frame for the 24 kDa polypeptide was inserted into the pET-28a(+) bacterial expression vector (see Materials and Methods) and the resulting 28 kDa fusion protein was expressed at high levels in *E. coli* (FIG. 4). Protein extracts prepared from *E. coli* expressing the recombinant protein produced a gel shift when a wild-type COR15a C-repeat/ DRE was used as probe (FIG. 5). No shift was detected with BSA or *E. coli* extracts prepared from strains harboring the vector alone, or the vector with an antisense insert for the 24 kDa polypeptide. Oligonucleotides encoding wild-type C-repeat/DRE sequences from COR15a or COR78 competed effectively for binding to the COR15a C-repeat/DRE probe, but mutant version of the COR15a C-repeat/DRE did not (FIG. 5). These in vitro results corroborated the in vivo yeast expression studies indicating that the 24 kDa polypeptide binds to the C-repeat/DRE sequence. The 24 kDa polypeptide was thus designated CBF1 (C-repeat/DRE binding factor 1) and the gene encoding it named CBF1.

Figure 6:
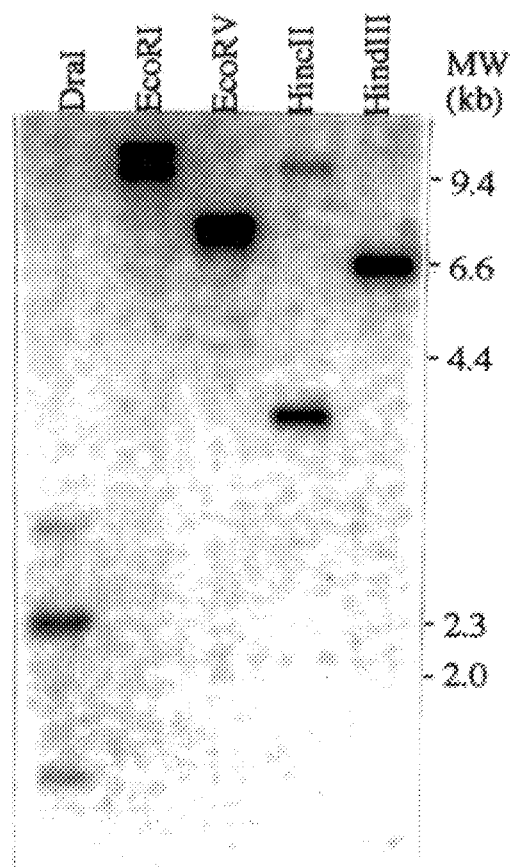

CBF1 is a unique or low copy number gene. The hybridization patterns observed in southern analysis of Arabidopsis DNA using the entire CBF1 gene as probe were relatively simple indicating that CBF1 is either a unique or low copy number gene (FIG. 6). The hybridization patterns obtained were not altered if only the 3' end of the gene was used as the probe (the EcoRV/BglII restriction fragment from pACT-11 encoding the acidic region of CBF1, but not the AP2 domain) or if hybridization was carried out at low stringency (not shown).

CBF1 transcript levels increase slightly in response to low temperature. Northern analysis indicated that the level of CBF1 transcripts increased about 2 to 3 fold in response to low temperature (FIG. 7B). In contrast, the transcript levels for COR15a increased approximately 35 fold in cold-treated plants (FIG. 7C). Only a singly hybridizing band was observed for CBF1 at either high or low stringency with probes for either the entire CBF1 coding sequence or the 3' end of the gene (the EcoRV/BglII fragment of pACT-11) (not shown). The size of the CBF1 transcripts was about 1.0 kb.

DISCUSSION

The C-repeat/DRE is a cis-acting regulatory element that stimulates transcription in response to low temperature (Yamaguchi-Shinozaki, K., et al., The Plant Cell 6:251–264 (1994); and Baker, S. S., et al., Plant Mol. Biol. 24:701–713 (1994); Jiang, C., et al., Plant Mol. Biol. 30:679–684 (1996)). In addition, at least certain versions of the element activate transcription in response to dehydration stress and high salinity (Yamaguchi-Shinozaki, K., et al., The Plant Cell 6:251–264 (1994)). Determining how the C-repeat/DRE stimulates gene expression in response to these environmental factors, and whether cold, dehydration and high salinity affect independent or overlapping regulatory systems, are key issues that need to be addressed. One step toward this end is determining the identity of protein factors that bind to the C-repeat/DRE. Here we described the first such protein, CBF1. We present evidence that CBF1 binds to the C-repeat/DRE both in vitro (gel shift assays) and in vivo (yeast expression assays). Further, the results demonstrate that CBF1 can activate transcription of reporter genes in yeast that contain the C-repeat/DRE. It thus seems probable that CBF1 binds to the C-repeat/DRE element in Arabidopsis plants and has a role in regulating transcription. Having available a cDNA clone for CBF1 makes possible a number of strategies to test this hypothesis such as altering the level of CBF1 in transgenic plants (e.g. "antisense" technology) and determining what effects this has on cold- and dehydration-regulated gene expression.

The results of the southern analysis indicate that CBF1 is a unique or low copy number gene in Arabidopsis. However, the CBF1 protein contains a 60 amino acid motif, the AP2 domain, that is evolutionary conserved in plants (Weigel, D., The plant Cell 7:388–389 (1995)). It is present in the APETALA2 (Jofuku, K. D., et al., The Plant Cell 6:1211–1225 (1994)), AINTEGUMENTA (Klucher, K. M., et al., the Plant Cell 8:137–153 (1996; and Elliot, R. C., et al., The Plant Cell 8:155–168 (1996)), TINY (Wilson, K., et al., The Plant Cell 8:659–671 (1996)) and cadmium-induced (Choi, S.-Y., et al., Plant Physiol. 108:849 (1995)) proteins of Arabidopsis and the EREBPs of tobacco (Ohme-Takagi, M. et al., The Plant Cell 7:173–182 (1995)). In addition, a search of the GenBank expressed sequence tagged cDNA database indicates that there is one cDNA from B. napus, two from Ricinus communis, and more than 25 from Arabidopsis and 15 from rice, that are deduced to encode proteins with AP2 domains. The results of Ohme-Takagi and Shinshi (Ohme-Takagi, M., et al., The Plant Cell 7:173–182 (1995)) indicate that the function of the AP2 domain is DNA-binding; this region of the putative tobacco transcription factor EREBP2 is responsible for its binding to the cis-acting ethylene response element referred to as the GCC-repeat. As discussed by Ohme-Takagi and Shinshi (Ohme-Takagi, M., et al., the Plant Cell 7:173–182 (1995)), the DNA-binding domain of EREBP2 (the AP2 domain) contains no significant amino acid sequence similarities or obvious structural similarities with other known transcription factors or DNA binding motifs. Thus, the domain appears to be a novel DNA-binding motif that to date, has only been found in plant proteins.

Presumably the binding of CBF1 to the C-repeat/DRE involves the AP2 domain. In this regard, it is germane to note that the tobacco ethylene response element, AGCCGCC, closely resembles the C-repeat/DRE sequences present in the promoters of the Arabidopsis genes COR15a, GGCCGAC, and COR78/RD29A, TACCGAC. An intriguing possibility thus raised is that CBF1, the EREBPs and perhaps other AP2 domain proteins are members of a superfamily of DNA binding proteins that recognize a family of cis-acting regulatory elements having, potentially, CCG as a common core sequence. The notion would be that differences in the sequence surrounding the CCG core element would result in recruitment of different AP2 domain proteins which, in turn, would be integrated into signal transduction pathways activated by different environmental, hormonal and developmental cues. Such a scenario is akin to the situation that exists for the ACGT-family of cis-acting elements (Foster et al., FASEB J. 8:192–200 (1994)). In this case, differences in the sequence surrounding the ACGT core element result in the recruitment of different bZIP transcription factors involved in activating transcription in response to a variety of environmental and developmental signals.

The results of the yeast transformation experiments indicate that CBF1 has a domain that can serve as a transcriptional activator. The most likely candidate for this domain is the acidic C-terminal half of the polypeptide. Indeed, random acidic amino acid peptides from E. coli have been shown to substitute for the GAL4 acidic activator domain of GAL4 in yeast (Ma, J. and M. Ptashne, Cell 51:113–199 (1987)). Moreover, acidic activator domains have been found to function across kingdoms (Hahn, S., Cell 72:481–483 (1993)); the yeast GAL4 acidic activator, for instance, can activate transcription in tobacco (Ma, J., et al., Nature 334:631–633 (1988)). It has also been shown that certain plant transcription factors, such as Vp1 (McCarty, D. R., et al., Cell 66:895–905 (1991)), have acidic domains that function as transcriptional activators in plants. Significantly, the acidic activation domains of the yeast transcription factors VP16 and GCN4 require the "adaptor" proteins ADA2, ADA3, and GCN5 for full activity (see Guarente, L., Trends Biochem. Sci. 20:517–521 (1995)). These proteins form a heteromeric complex (Horiuchi, J., et al., Mol. Cell Biol. 15:1203–1209 (1995)) that bind to the relevant activation domains. The precise mechanism of transcriptional activation is not known, but appears to involve histone acetylation: there is a wealth of evidence showing a positive correlation between histone acetylation and the transcriptional activity of chromatin (Wolffe, A. P., Trends Biochem. Sci. 19:240–244 (1994)) and recently, the GCN5 protein has been shown to have histone acetyltransferase activity (Brownell, J. E., et al., Cell 84:843–851 (1996)). Genetic studies indicate that CBF1, like VP16 and GCN4, requires ADA2, ADA3 and GCN5 to function optimally in yeast. The fundamental question thus raised is whether plants have homologs of ADA2. ADA3 and GCN5 and whether these adaptors are required for CBF1 function (and function of other transcription factors with acidic activator regions) in Arabidopsis.

A final point regards regulation of CBF1 activity. The results of the northern analysis indicate that CBF1 transcript levels increase only slightly in response to low temperature, while those for COR15a increase dramatically (FIG. 7). Thus, unlike in yeast, it would appear that transcription of CBF1 in Arabidopsis at warm temperatures is not sufficient to cause appreciable activation of promoters containing the C-repeat/DRE. The molecular basis for this apparent low temperature activation of CBF1 in Arabidopsis is not known. One intriguing possibility, however is that CBF1 might be modified at low temperature in Arabidopsis resulting in either stabilization of the protein, translocation of the protein from the cytoplasm to the nucleus, or activation of either the DNA binding domain or activation domain of the protein. Such modification could involve a signal transduction pathway that is activated by low temperature. Indeed, as already discussed, cold-regulated expression of COR genes in Arabidopsis and alfalfa appears to involve a signal transduction pathway that is activated by low temperature-induced calcium flux (Knight, H., et al., The Plant Cell 8:489–503 (1996); Knight, M. R., et al., Nature 352:524–526 (1991); Monroy, A. F., et al, Plant Physiol. 102:1227–1235 (1993); Monroy, A. F., and R. S., The Plant Cell, 7:321–331 (1995)). It will, therefore, be of interest to determine whether CBF1 is modified at low temperature, perhaps by phosphorylation, and if so, whether this is dependent on calcium-activated signal transduction.

EXAMPLE 2
Use of CBF1 to Improve Plant Stress Tolerance

Many plants increase in freezing tolerance in response to low non-freezing temperatures, a process known as cold acclimation. A large number of biochemical changes occur during cold acclimation including the activation of COR genes. These genes, which are also expressed in response to dehydration (e.g., drought and high salinity), are thought to help protect plant cells against the potentially deleterious effects of dehydration associated with freezing, drought and high salinity stress. Indeed, expression of the COR15a gene in plants grown at normal temperatures (22° C.) enhances the freezing tolerance of chloroplasts.

By manipulating the expression of COR genes, the stress tolerance of crop and horticultural plants are improved, e.g., engineer broader climate ranges; target stress resistance to stress-sensitive parts of plants; render plants stress-resistant when a stress condition (frost and drought) is imminent. To bring about these effects, however, the expression of the COR genes must be manipulated. The gene, CBF1, that encodes the transcription factor that binds to the C-repeat/DRE regulatory element present in the promoters of all COR genes described to date has been isolated. CBF1 in yeast activates expression of reporter genes that have been fused to the C-repeat/DRE element. Thus, expression of CBF1 in plants can activate expression of COR genes.

By introducing modified versions of CBF1 into plants, the expression of COR genes can be modified, and thereby enhance the freezing and dehydration tolerance of plants. One potentially useful modification of CBF1 is to place the gene under the control of a strong constitutive promoter. This leads to increased levels of COR gene expression in both non-stress and stressed plants which in turn, results in enhanced freezing and dehydration tolerance. Other potential useful modifications are to place CBF1 under a tissue specific promoter to alter COR gene expression in tissues that are highly sensitive to stress (and thereby enhance the stress tolerance of these tissues); to place CBF1 under control of an inducible promoter such that COR gene expression could be induced by application of an exogenous inducer (e.g., induce COR genes when a frost is imminent); and modify the activation domain of the CBF1 protein to alter the temperature and dehydration range over which it activates COR gene expression. In all of these experiments, modified CBF1 genes are transformed into the plant of interest to modify expression of the endogenous COR genes. Of course, it is also possible to transform into plants various genes fused to the C-repeat/DRE element and control the expression of these genes through the action of CBF1.

We claim:

1. DNA in isolated form encoding a protein comprising an amino acid sequence sufficiently homologous to an AP2 domain of SEQ. ID. No. 2 that the protein binds to a cold or dehydration transcription regulating region comprising a sequence CCG.

2. DNA according to claim 1 wherein the amino acid sequence comprises the AP2 domain of SEQ. ID. No.2.

3. DNA according to claim 1 wherein the protein is capable of binding to a cold or dehydration transcription regulating region comprising a sequence CCGAC.

4. DNA according to claim 1 wherein the protein is capable of binding to a cold or dehydration transcription regulating region comprising a sequence selected from the group consisting of SEQ. ID. Nos. 3, 7, 8, and 9.

5. DNA according to claim 1 wherein the protein is capable of binding to a cold or dehydration transcription regulating region of *Arabidopsis thaliana* or a homologous regulatory region of another plant species.

6. DNA in isolated from comprising nucleotides 159 to 797 of SEQ ID NO:1.

7. DNA in isolated form comprising a sequence encoding a protein comprising an amino add sequence sufficiently homologous to SEQ. ID. No. 2 that the protein binds to a cold or dehydration transcription regulating region comprising a sequence CCG.

8. DNA according to claim 7 wherein the protein is capable of binding to a cold or dehydration transcription regulating region comprising a sequence CCGAC.

9. DNA according to claim 7 wherein the protein is capable of binding to a cold or dehydration transcription regulating region comprising a sequence selected from the group consisting of SEQ. ID. Nos. 3, 7, 8, and 9.

10. DNA according to claim 7 wherein the protein is capable of binding to a cold or dehydration transcription regulating region of *Arabidopsis thaliana* or a homologous regulatory region of another plant species.

11. DNA in isolated form encoding an amino acid sequence set forth in SEQ ID NO:2.

12. A plasmid encoding a protein comprising an amino add sequence sequence sufficiently homologous to an AP2 domain of SEQ. ID. No.2 that the protein binds to a cold or dehydration transcription regulating region comprising a sequence CCG.

13. A plasmid according to claim 12 wherein the amino acid sequence comprises the AP2 domain of SEQ. ID. No. 2.

14. A plasmid according to claim 12 wherein the protein is capable of binding to a cold or dehydration transcription regulating region comprising a sequence CCGAC.

15. A plasmid according to claim 12 wherein the protein is capable of binding to a cold or dehydration transcription regulating region comprising a sequence selected from the group consisting of SEQ. ID. Nos. 3, 7, 8, and 9.

16. A plasmid according to claim 12 wherein the protein is capable of binding to a cold or dehydration transcription regulating region comprising of *Arabidopsis thaliana* or a homologous regulatory region of another plant species.

17. A plasmid comprising nucleotides 159 to 797 of SEQ ID No. 1.

18. A plasmid comprising a sequence encoding a protein comprising an amino acid sequence sufficiently homologous to SEQ. ID. No. 2 that the protein binds to a cold or dehydration transcription regulating region comprising a sequence CCG.

19. A plasmid according to claim 18 wherein the protein is capable of binding to a cold or dehydration transcription regulating region comprising a sequence CCGAC.

20. A plasmid according to claim 18 wherein the protein is capable of binding to a cold or dehydration transcription regulating region comprising a sequence selected from the group consisting of SEQ. ID. Nos. 3, 7, 8, and 9.

21. A plasmid according to claim 18 wherein the protein is capable of binding to a cold or dehydration transcription regulating region of *Arabidopsis thaliana* or an essentially homologous regulatory region of another plant species.

22. A plasmid encoding an amino acid sequence set forth in SEQ ID No. 2.

23. A plasmid deposited as ATCC 98063.

24. A DNA construct capable of transforming a cell comprising a nucleic acid sequence encoding an amino acid sequence sufficiently homologous to an AP2 domain of SEQ. ID. No. 2 that the protein binds to a cold or dehydration transcription regulating region comprising a sequence CCG.

25. A DNA construct according to claim 24 wherein the amino acid sequence comprises the AP2 domain of SEQ. ID. No. 2.

26. A DNA construct according to claim 24 wherein the protein is capable of binding to a cold or dehydration transcription regulating region comprising a sequence CCGAC.

27. A DNA construct according to claim 24 wherein the protein is capable of binding to a cold or dehydration transcription regulating region comprising a sequence selected from the group consisting of SEQ. ID. Nos. 3, 7, 8, and 9.

28. A DNA construct according to claim 24 wherein the protein is capable of binding to a cold or dehydration transcription regulating region of *Arabidopsis thaliana* or an essentially homologous regulatory region of another plant species.

29. A DNA construct capable of transforming a cell comprising nucleotides 159 to 797 of SEQ ID No. 1.

30. A DNA construct capable of transforming a cell comprising a nucleic acid sequence encoding an amino acid sequence sufficiently homologous to SEQ. ID. No. 2 that the protien binds to a cold or dehydration transcription regulating region comprising a sequence CCG.

31. A DNA construct according to claim 30 wherein the protein is capable of binding to a cold or dehydration transcription regulating region comprising a sequence CCGAC.

32. A DNA construct according to claim 30 wherein the protein is capable of binding to a cold or dehydration transcription regulating region comprising a sequence selected from the group consisting of SEQ. ID. Nos. 3, 7, 8, and 9.

33. A DNA construct according to claim 30 wherein the protein is capable of binding to a cold or dehydration transcription regulating region of *Arabidopsis thaliana* or an essentially homologous regulatory region of another plant species.

34. A DNA construct encoding an amino acid sequence set forth in SEQ ID No. 2.

35. A cell comprising a transformed sequence encoding an amino acid sequence sufficiently homologous to an AP2 domain of SEQ. ID. No. 2 that the protein binds to a cold or dehydration transcription regulating region comprising a sequence CCG.

36. A cell according to claim 35 wherein the amino acid sequence comprises the AP2 domain of SEQ. ID. No. 2.

37. A cell according to claim 35 wherein the protein is capable of binding to a cold or dehydration transcription regulating region comprising a sequence CCGAC.

38. A cell according to claim 35 wherein the protein is capable of binding to a cold or dehydration transcription regulating region comprising a sequence selected from the group consisting of SEQ. ID. Nos. 3, 7, 8, and 9.

39. A cell according to claim 35 wherein the protein is capable of binding to a cold or dehydration transcription regulating region of *Arabidopsis thaliana* or an essentially homologous regulatory region of another plant species.

40. A cell according to claim 35 wherein the cell is a microorganism.

41. A cell according to claim 35 wherein the microorganism is *Escherichia coli*.

42. A cell according to claim 35 wherein the microorganism is *Saccharomyces cerevisiae*.

43. A cell comprising a transformed sequence which comprises nucleotides 159 to 797 of SEQ ID. No. 1.

44. A cell comprising a transformed sequence encoding an amino acid sequence sufficiently homologous to SEQ. ID. No. 2 that the protein binds to a cold or dehydration transcription regulating region comprising a sequence CCG.

45. A cell according to claim 44 wherein the amino acid sequence comprises an AP2 domain of SEQ. ID. No. 2.

46. A cell according to claim 44 wherein the protein is capable of binding to a cold or dehydration transcription regulating region comprising a sequence CCGAC.

47. A cell according to claim 44 wherein the protein is capable of binding to a cold or dehydration transcription regulating region comprising a sequence selected from the group consisting of SEQ. ID. Nos. 3, 7, 8, and 9.

48. A cell according to claim 44 wherein the protein is capable of binding to a cold or dehydration transcription regulating region of *Arabidopsis thaliana* or a homologous regulatory region of another plant species.

49. A cell comprising a transformed sequence encoding an amino acid sequence set forth in SEQ ID No. 2.

\* \* \* \* \*